US011579837B2

(12) United States Patent
Robinson et al.

(10) Patent No.: US 11,579,837 B2
(45) Date of Patent: *Feb. 14, 2023

(54) AUDIO PROFILE FOR PERSONALIZED AUDIO ENHANCEMENT

(71) Applicant: META PLATFORMS TECHNOLOGIES, LLC, Menlo Park, CA (US)

(72) Inventors: Philip Robinson, Seattle, WA (US); Antonio John Miller, Woodinville, WA (US); William Owen Brimijoin, II, Kirkland, WA (US); Andrew Lovitt, Redmond, WA (US)

(73) Assignee: Meta Platforms Technologies, LLC, Menlo Park, CA (US)

(*) Notice: Subject to any disclaimer, the term of this patent is extended or adjusted under 35 U.S.C. 154(b) by 90 days.

This patent is subject to a terminal disclaimer.

(21) Appl. No.: 17/196,725

(22) Filed: Mar. 9, 2021

(65) Prior Publication Data

US 2021/0216271 A1 Jul. 15, 2021

Related U.S. Application Data

(63) Continuation of application No. 16/562,879, filed on Sep. 6, 2019, now Pat. No. 10,976,991.

(Continued)

(51) Int. Cl.
*G06F 3/16* (2006.01)
*G06F 21/62* (2013.01)
*G10L 25/51* (2013.01)

(52) U.S. Cl.
CPC .......... *G06F 3/165* (2013.01); *G06F 21/6245* (2013.01); *G10L 25/51* (2013.01)

(58) Field of Classification Search
CPC .... H04R 25/70; H04R 3/005; H04R 2420/07; H04R 3/00; H04R 1/406; H04R 25/505; H04R 25/554; H04R 27/00; H04R 1/1041; H04R 2225/55; H04R 2225/43; H04R 2225/41; H04R 3/12; H04R 25/50; H04R 2499/11; H04R 5/04; H04R 1/028; H04R 3/04; H04R 2430/01; H04R 25/558; H04R 2499/13; H04R 1/1083; H04R 25/552; H04R 2227/005; H04R 1/08; H04R 5/033;

(Continued)

(56) References Cited

U.S. PATENT DOCUMENTS 8,572,493 B2 10/2013 Qureshi
10,680,995 B1* 6/2020 Hinkle ................ H04L 12/1813
(Continued)

OTHER PUBLICATIONS

PCT International Search Report and Written Opinion, PCT Application No. PCT/US2020/032304, dated Aug. 6, 2020, 11 pages.

*Primary Examiner* — Lun-See Lao
(74) *Attorney, Agent, or Firm* — Fenwick & West LLP

(57) ABSTRACT

A system creates an audio profile. The audio profile may be stored in a database. For example, the audio profile may be securely stored in a database of a social network and associated with a user account. The audio profile may contain data describing the way in which the specific user hears and interprets sounds. Systems and applications which present sounds to the user may access the audio profile and modify the sounds presented to the user based on the data in the audio profile to enhance the audio experience for the user.

20 Claims, 5 Drawing Sheets

Related U.S. Application Data

(60) Provisional application No. 62/857,410, filed on Jun. 5, 2019.

(58) Field of Classification Search
CPC ............ H04R 1/1016; H04R 2227/003; H04R 25/30; H04R 25/407; H04R 2430/20; H04R 2460/13; H04R 2430/03; H04R 25/305; H04R 3/02; H04R 29/001; H04R 1/1091; H04R 29/00; H04R 2201/107; H04R 2225/61; H04R 2410/05; H04R 2225/39; H04R 2460/01; H04R 25/00; H04R 2201/401; H04R 25/606; H04R 29/004; H04R 25/453; H04R 1/02; H04R 2420/01; H04R 2499/15; H04R 5/02; H04R 2460/07; H04R 1/326; H04R 25/43; H04R 25/356; H04R 1/1008; H04R 2460/03; H04R 2430/23; H04R 25/55; H04R 2410/07; H04R 29/005; H04R 2225/67; H04R 2410/01; H04R 25/405; H04R 2225/025; H04R 1/025; H04R 1/1025; H04R 5/027; H04R 25/603; H04R 2420/05; H04R 3/002; H04R 1/403; H04R 1/04; H04R 29/007; H04R 2201/403; H04R 2420/09; H04R 2225/51; H04R 25/353; H04R 25/604; H04R 2420/03; H04R 25/507; H04R 25/75; H04R 1/083
USPC ................................ 381/56–58, 1–3; 700/94
See application file for complete search history.

(56) References Cited

U.S. PATENT DOCUMENTS

| | | | |
|---|---|---|---|
| 10,976,991 B2* | 4/2021 | Robinson | G16H 20/30 |
| 2003/0128859 A1 | 7/2003 | Greene et al. | |
| 2012/0183164 A1 | 7/2012 | Foo et al. | |
| 2013/0322708 A1 | 12/2013 | Heringslack | |
| 2015/0019982 A1* | 1/2015 | Petitt, Jr | G06F 21/00 |
| | | | 715/738 |
| 2016/0246367 A1* | 8/2016 | Tungare | G06F 3/0237 |
| 2017/0272890 A1 | 9/2017 | Oh et al. | |
| 2018/0124495 A1* | 5/2018 | Boesen | H04R 3/04 |
| 2018/0130459 A1* | 5/2018 | Paradiso | G10L 13/04 |
| 2018/0227682 A1 | 8/2018 | Lederman | |
| 2018/0324541 A1* | 11/2018 | Pang | H04S 1/005 |
| 2019/0030277 A1 | 1/2019 | Espi Maques et al. | |
| 2019/0261102 A1* | 8/2019 | Foo | G06F 40/58 |
| 2021/0405962 A1* | 12/2021 | Mackay | H04N 21/4305 |

\* cited by examiner

AUDIO PROFILE FOR PERSONALIZED AUDIO ENHANCEMENT

CROSS-REFERENCE TO RELATED APPLICATIONS

This application is a continuation of U.S. patent application Ser. No. 16/562,879, filed Sep. 6, 2019, which claims the benefit of U.S. Provisional Application No. 62/857,410 filed Jun. 5, 2019, which is incorporated by reference in its entirety.

FIELD OF THE INVENTION

The present disclosure generally relates to audio systems, and specifically relates to providing customized audio content.

BACKGROUND

People hear sounds differently. For users of an audio system, such as an audio system in an artificial reality system, the sounds presented by the audio system may be heard differently by different users. For example, some users may have hyperacusis (excessive sensitivity), presbyacusis (insensitivity to some frequencies), or some other condition that affects how they perceive sound. Accordingly, hearing differences among different users can affect their perception of presented audio content.

SUMMARY

A wearable device performs an audio assessment for a user. Based on the results of the audio assessment, the wearable device creates an audio profile. The audio profile may be stored in a database. For example, the audio profile may be stored in a database of a social network and associated with a user account. The audio profile may contain data describing the way in which the specific user hears and interprets sounds. For example, many users have difficulty understanding speech in highly reverberant environments. Systems and applications which present sounds to the user may access the audio profile and modify the sounds presented to the user based on the data in the audio profile to enhance the audio experience for the user.

In some embodiments, systems, methods, and computer program product may perform operations including collecting, by an audio system on a wearable device, audio assessment data for a user. The audio assessment data may be collected using active and/or passive audio assessment routines. The audio system creates an audio profile based on the audio assessment data and physical data describing the user. The audio system may store the audio profile locally on the wearable device or transmit the audio file to an external system, such as a social network. The audio system presents audio content to the user based in part on the audio profile.

Figure 1A:
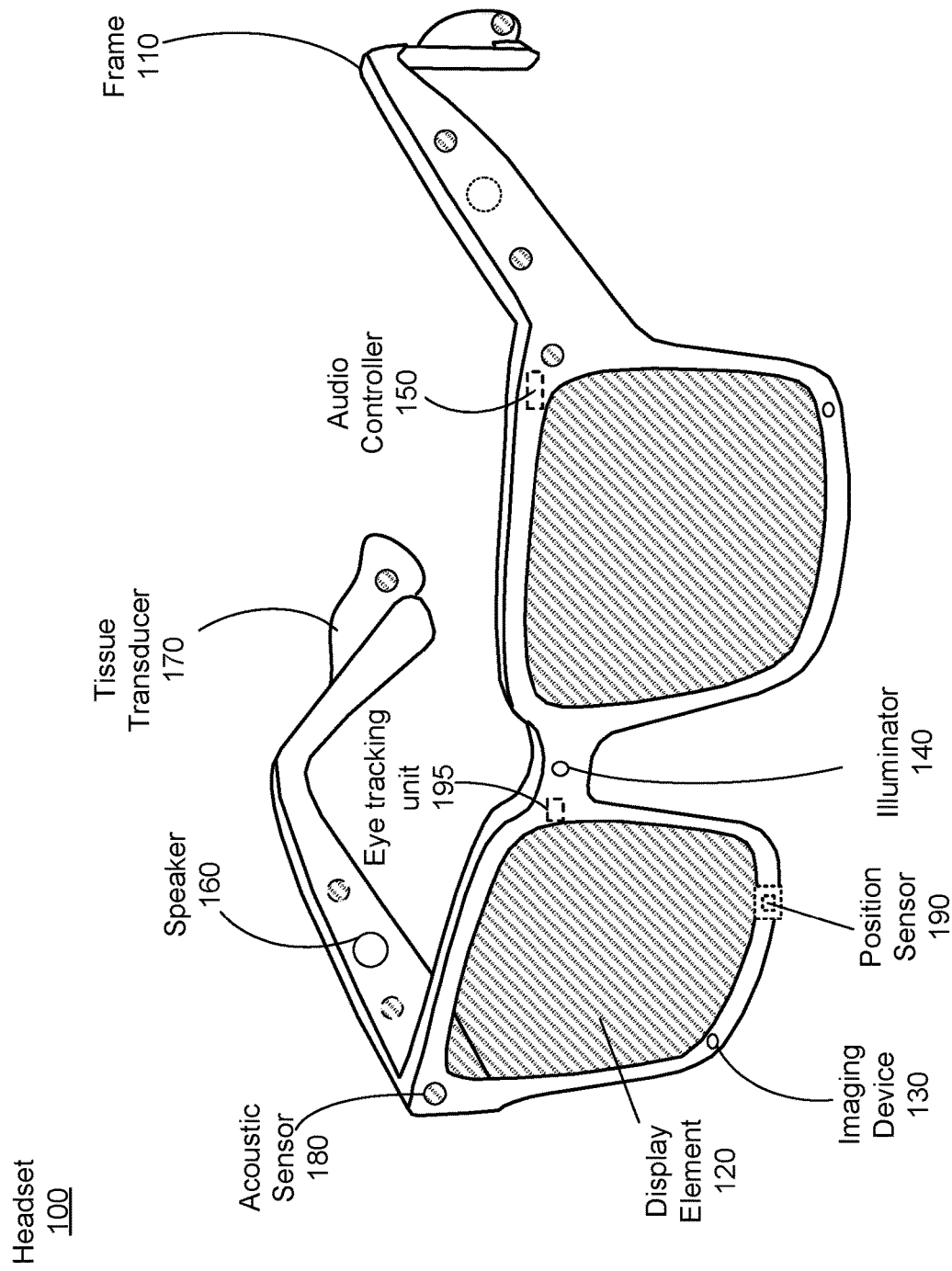
FIG. 1A is a perspective view of a headset implemented as an eyewear device, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

A system provides personalized audio content to a user to enhance the audio experience of the user. A wearable device, such as a headset or a smart watch, may conduct an audio assessment for a user. For example, the wearable device may present the user with audio games, an audiology screen, listening tests, momentary environmental assessments, and post experience surveys. The wearable device may monitor the behavior of the user in response to audio content, such as the direction of eye gaze in response to a sound, whether the user reacted to a sound, whether the user understood the speech in audio content, etc. The system may create an audio profile. The audio profile may be stored in a database. For example, the audio profile may be stored in a database of a social network and associated with a user account. The audio profile may contain data describing the way in which the specific user hears and interprets sounds. Systems and applications which present sounds to the user may access the audio profile and modify the sounds presented to the user based on the data in the audio profile to enhance the audio experience for the user. For example, if a user has hyperacusis to frequencies between 10 kHz-15 kHz, the amplitude of sounds in that frequency band can be decreased for the user.

Traditional audiological screening can give an understanding of pure tone audibility thresholds, but such assessments are done in absolute quiet and do not necessarily give insight into how a listener will perceive or perform in a real environment. The systems and methods described herein monitor and assess a user's hearing performance in realistic scenarios. Additionally, these routines can be combined with other results related to physical characteristics of the user, such as personalized Head-Related Transfer Functions and Body-Related Transfer Functions, to generate the unique individual audio profile. Once the audio profile is established, it may be attached and maintained as part of the user's social network profile. The audio profile may be encrypted or otherwise secured to protect medical data of the user. The system may prompt the user for permission to store the audio profile, and the system may allow the user to select who may access the audio profile. The audio profile may be accessed to improve the audio across all of the user's audio experiences, including video calling, virtual reality games and applications, augmented reality telepresence, real-time speech enhancement, real-time noise reduction, etc.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world)

content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to create content in an artificial reality and/or are otherwise used in an artificial reality. The artificial reality system that provides the artificial reality content may be implemented on various platforms, including a wearable device (e.g., headset) connected to a host computer system, a standalone wearable device (e.g., headset), a mobile device or computing system, or any other hardware platform capable of providing artificial reality content to one or more viewers.

FIG. 1A is a perspective view of a headset 100 implemented as an eyewear device, in accordance with one or more embodiments. In some embodiments, the eyewear device is a near eye display (NED). In general, the headset 100 may be worn on the face of a user such that content (e.g., media content) is presented using a display assembly and/or an audio system. However, the headset 100 may also be used such that media content is presented to a user in a different manner. Examples of media content presented by the headset 100 include one or more images, video, audio, or some combination thereof. The headset 100 includes a frame, and may include, among other components, a display assembly including one or more display elements 120, a depth camera assembly (DCA), an audio system, and a position sensor 190. While FIG. 1A illustrates the components of the headset 100 in example locations on the headset 100, the components may be located elsewhere on the headset 100, on a peripheral device paired with the headset 100, or some combination thereof. Similarly, there may be more or fewer components on the headset 100 than what is shown in FIG. 1A.

The frame 110 holds the other components of the headset 100. The frame 110 includes a front part that holds the one or more display elements 120 and end pieces (e.g., temples) to attach to a head of the user. The front part of the frame 110 bridges the top of a nose of the user. The length of the end pieces may be adjustable (e.g., adjustable temple length) to fit different users. The end pieces may also include a portion that curls behind the ear of the user (e.g., temple tip, ear piece).

The one or more display elements 120 provide light to a user wearing the headset 100. As illustrated the headset includes a display element 120 for each eye of a user. In some embodiments, a display element 120 generates image light that is provided to an eyebox of the headset 100. The eyebox is a location in space that an eye of user occupies while wearing the headset 100. For example, a display element 120 may be a waveguide display. A waveguide display includes a light source (e.g., a two-dimensional source, one or more line sources, one or more point sources, etc.) and one or more waveguides. Light from the light source is in-coupled into the one or more waveguides which outputs the light in a manner such that there is pupil replication in an eyebox of the headset 100. In-coupling and/or outcoupling of light from the one or more waveguides may be done using one or more diffraction gratings. In some embodiments, the waveguide display includes a scanning element (e.g., waveguide, mirror, etc.) that scans light from the light source as it is in-coupled into the one or more waveguides. Note that in some embodiments, one or both of the display elements 120 are opaque and do not transmit light from a local area around the headset 100. The local area is the area surrounding the headset 100. For example, the local area may be a room that a user wearing the headset 100 is inside, or the user wearing the headset 100 may be outside and the local area is an outside area. In this context, the headset 100 generates VR content. Alternatively, in some embodiments, one or both of the display elements 120 are at least partially transparent, such that light from the local area may be combined with light from the one or more display elements to produce AR and/or MR content.

In some embodiments, a display element 120 does not generate image light, and instead is a lens that transmits light from the local area to the eyebox. For example, one or both of the display elements 120 may be a lens without correction (non-prescription) or a prescription lens (e.g., single vision, bifocal and trifocal, or progressive) to help correct for defects in a user's eyesight. In some embodiments, the display element 120 may be polarized and/or tinted to protect the user's eyes from the sun.

Note that in some embodiments, the display element 120 may include an additional optics block (not shown). The optics block may include one or more optical elements (e.g., lens, Fresnel lens, etc.) that direct light from the display element 120 to the eyebox. The optics block may, e.g., correct for aberrations in some or all of the image content, magnify some or all of the image, or some combination thereof.

The display element 120 may display content as part of an audio assessment routine. For example, the display element 120 may display instructions or provide feedback to the user during the audio assessment routine.

The DCA determines depth information for a portion of a local area surrounding the headset 100. The DCA includes one or more imaging devices 130 and a DCA controller (not shown in FIG. 1A), and may also include an illuminator 140. In some embodiments, the illuminator 140 illuminates a portion of the local area with light. The light may be, e.g., structured light (e.g., dot pattern, bars, etc.) in the infrared (IR), IR flash for time-of-flight, etc. In some embodiments, the one or more imaging devices 130 capture images of the portion of the local area that include the light from the illuminator 140. As illustrated, FIG. 1A shows a single illuminator 140 and two imaging devices 130. In alternate embodiments, there is no illuminator 140 and at least two imaging devices 130.

The DCA controller computes depth information for the portion of the local area using the captured images and one or more depth determination techniques. The depth determination technique may be, e.g., direct time-of-flight (ToF) depth sensing, indirect ToF depth sensing, structured light, passive stereo analysis, active stereo analysis (uses texture added to the scene by light from the illuminator 140), some other technique to determine depth of a scene, or some combination thereof.

The DCA controller may, in combination with the audio system, determine the location of one or more sound sources in a local scene. The DCA controller may provide the locations of objects in the local scene. The DCA may provide the locations of the objects to the audio system. The audio system may determine that a sound source emanating from the same direction of an object located by the DCA may be caused by the object. The audio system may subsequently use the determined locations of the sound sources in conjunction with an audio assessment routine.

The audio system provides audio content. The audio system includes a transducer array, a sensor array, and an audio controller 150. However, in other embodiments, the audio system may include different and/or additional components. Similarly, in some cases, functionality described with reference to the components of the audio system can be distributed among the components in a different manner than is described here. For example, some or all of the functions of the controller may be performed by a remote server.

The audio system may conduct an audio assessment routine for a user. The audio assessment routine is a series of steps by which the audio system determines parameters describing the characteristics of a user's hearing, such as hyperacusis or presbyacusis to certain frequencies, acceptable reverberation levels, etc. The audio assessment routine may include monitoring user responses with various sensors on the headset 100, such as the imaging device 130, the acoustic sensor 180, or the position sensor 190. The audio system creates an audio profile for the user based on the parameters. The audio profile is a set of parameters that describes how the user hears sounds. The audio system may use the audio profile to modify sounds presented to the user.

The transducer array presents sound to user. The transducer array includes a plurality of transducers. A transducer may be a speaker 160 or a tissue transducer 170 (e.g., a bone conduction transducer or a cartilage conduction transducer). Although the speakers 160 are shown exterior to the frame 110, the speakers 160 may be enclosed in the frame 110. In some embodiments, instead of individual speakers for each ear, the headset 100 includes a speaker array comprising multiple speakers integrated into the frame 110 to improve directionality of presented audio content. The tissue transducer 170 couples to the head of the user and directly vibrates tissue (e.g., bone or cartilage) of the user to generate sound. The number and/or locations of transducers may be different from what is shown in FIG. 1A.

The sensor array detects sounds within the local area of the headset 100. The sensor array includes a plurality of acoustic sensors 180. An acoustic sensor 180 captures sounds emitted from one or more sound sources in the local area (e.g., a room). Each acoustic sensor is configured to detect sound and convert the detected sound into an electronic format (analog or digital). The acoustic sensors 180 may be acoustic wave sensors, microphones, sound transducers, or similar sensors that are suitable for detecting sounds.

In some embodiments, one or more acoustic sensors 180 may be placed in an ear canal of each ear (e.g., acting as binaural microphones). In some embodiments, the acoustic sensors 180 may be placed on an exterior surface of the headset 100, placed on an interior surface of the headset 100, separate from the headset 100 (e.g., part of some other device), or some combination thereof. The number and/or locations of acoustic sensors 180 may be different from what is shown in FIG. 1A. For example, the number of acoustic detection locations may be increased to increase the amount of audio information collected and the sensitivity and/or accuracy of the information. The acoustic detection locations may be oriented such that the microphone is able to detect sounds in a wide range of directions surrounding the user wearing the headset 100.

The audio controller 150 processes information from the sensor array that describes sounds detected by the sensor array. The audio controller 150 may comprise a processor and a computer-readable storage medium. The audio controller 150 may be configured to generate direction of arrival (DOA) estimates, generate acoustic transfer functions (e.g., array transfer functions and/or head-related transfer functions), track the location of sound sources, form beams in the direction of sound sources, classify sound sources, generate sound filters for the speakers 160, or some combination thereof.

The position sensor 190 generates one or more measurement signals in response to motion of the headset 100. The position sensor 190 may be located on a portion of the frame 110 of the headset 100. The position sensor 190 may include an inertial measurement unit (IMU). Examples of position sensor 190 include: one or more accelerometers, one or more gyroscopes, one or more magnetometers, another suitable type of sensor that detects motion, a type of sensor used for error correction of the IMU, or some combination thereof. The position sensor 190 may be located external to the IMU, internal to the IMU, or some combination thereof.

In some embodiments, the headset 100 may provide for simultaneous localization and mapping (SLAM) for a position of the headset 100 and updating of a model of the local area. For example, the headset 100 may include a passive camera assembly (PCA) that generates color image data. The PCA may include one or more RGB cameras that capture images of some or all of the local area. In some embodiments, some or all of the imaging devices 130 of the DCA may also function as the PCA. The images captured by the PCA and the depth information determined by the DCA may be used to determine parameters of the local area, generate a model of the local area, update a model of the local area, or some combination thereof. Furthermore, the position sensor 190 tracks the position (e.g., location and pose) of the headset 100 within the room. Additional details regarding the components of the headset 100 are discussed below in connection with FIG. 4.

The headset 100 comprises an eye tracking unit 195. The eye tracking unit 195 may include one or cameras which capture images of the user's eyes. The eye tracking unit 195 may further comprise one or more illuminators that illuminate the user's eyes. The eye tracking unit 195 estimates the angular orientation of the user's eye or eyes. In some embodiments, the eye tracking unit 195 may detect distortions in an illumination pattern projected by the illuminators to determine the angular orientation of the user's eyes. The orientation of the eyes corresponds to the direction of the user's gaze within the headset 100. The orientation of the user's eye may be the direction of the foveal axis, which is the axis between the fovea (an area on the retina of the eye with the highest concentration of photoreceptors) and the center of the eye's pupil. In general, when a user's eyes are fixed on a point, the foveal axes of the user's eyes intersect that point. The pupillary axis is another axis of the eye which is defined as the axis passing through the center of the pupil which is perpendicular to the corneal surface. The pupillary axis does not, in general, directly align with the foveal axis. Both axes intersect at the center of the pupil, but the orientation of the foveal axis is offset from the pupillary axis by approximately −1° to 8° laterally and ±4° vertically. Because the foveal axis is defined according to the fovea, which is located in the back of the eye, the foveal axis can be difficult or impossible to detect directly in some eye tracking embodiments. Accordingly, in some embodiments, the orientation of the pupillary axis is detected and the foveal axis is estimated based on the detected pupillary axis. However, in some embodiments the orientation of the pupillary axis may be used to estimate the angular orientation of the user's eye or eyes without adjusting for the foveal axis difference.

In general, movement of an eye corresponds not only to an angular rotation of the eye, but also to a translation of the eye, a change in the torsion of the eye, and/or a change in shape of the eye. The eye tracking unit 195 may also detect translation of the eye: i.e., a change in the position of the eye relative to the eye socket. In some embodiments, the translation of the eye is not detected directly, but is approximated based on a mapping from a detected angular orientation. Translation of the eye corresponding to a change in the eye's position relative to the detection components of the eye tracking unit may also be detected. Translation of this type may occur, for example, due to shift in the position of the headset 100 on a user's head. The eye tracking unit 195 may also detect the torsion of the eye, i.e., rotation of the eye about the pupillary axis. The eye tracking unit 195 may use the detected torsion of the eye to estimate the orientation of the foveal axis from the pupillary axis. The eye tracking unit 195 may also track a change in the shape of the eye, which may be approximated as a skew or scaling linear transform or a twisting distortion (e.g., due to torsional deformation). The eye tracking unit 195 may estimate the foveal axis based on some combination of the angular orientation of the pupillary axis, the translation of the eye, the torsion of the eye, and the current shape of the eye.

In some embodiments, the eye tracking unit 195 may include at least one emitter which projects a structured light pattern on all or a portion of the eye. This pattern then is then projected onto to the shape of the eye, which may produce a perceived distortion in the structured light pattern when viewed from an offset angle. The eye tracking unit 195 may also include at least one camera which detects the distortions (if any) of the light pattern projected onto the eye. A camera, oriented on a different axis than the emitter, captures the illumination pattern on the eye. This process is denoted herein as "scanning" the eye. By detecting the deformation of the illumination pattern on the surface of the eye, the eye tracking unit 195 can determine the shape of the portion of the eye scanned. The captured distorted light pattern is therefore indicative of the 3D shape of the illuminated portion of the eye. By deriving the 3D shape of the portion of the eye illuminated by the emitter, the orientation of the eye can be derived. The eye tracking unit can also estimate the pupillary axis, the translation of the eye, the torsion of the eye, and the current shape of the eye based on the image of the illumination pattern captured by the camera.

In other embodiments, any suitable type of eye tracking system may be utilized. For example, the eye tracking unit 195 may capture images of the eyes, capture stereo images of the eyes, may utilize a ring of LEDs around the eyes which emit light in a sequence and determine eye orientation based on reflections from the LEDs, may utilize time-of-flight measurements, etc.

As the orientation may be determined for both eyes of the user, the eye tracking unit 195 is able to determine where the user is looking. The headset 100 can use the orientation of the eye to, e.g., determine an inter-pupillary distance (IPD) of the user, determine gaze direction, introduce depth cues (e.g., blur image outside of the user's main line of sight), collect heuristics on the user interaction in the VR media (e.g., time spent on any particular subject, object, or frame as a function of exposed stimuli), some other function that is based in part on the orientation of at least one of the user's eyes, or some combination thereof. Determining a direction of a user's gaze may include determining a point of convergence based on the determined orientations of the user's left and right eyes. A point of convergence may be the point that the two foveal axes of the user's eyes intersect (or the nearest point between the two axes). The direction of the user's gaze may be the direction of a line through the point of convergence and though the point halfway between the pupils of the user's eyes. Additional details regarding the components of the headset 100 are discussed below in connection with FIG. 4.

The audio system generates an audio profile for the user. The audio system monitors user responses to sounds. The eye tracking unit 195 detects a gaze location of the user's eyes in response to the sounds. The audio system measures an accuracy of various parameters for the sounds based on user responses, such as differences between the gaze locations and the sound source locations. The audio system uses the audio profile to subsequently present enhanced audio content to the user. The audio enhancement process is further described with reference to FIGS. 2-4.

Figure 1B:
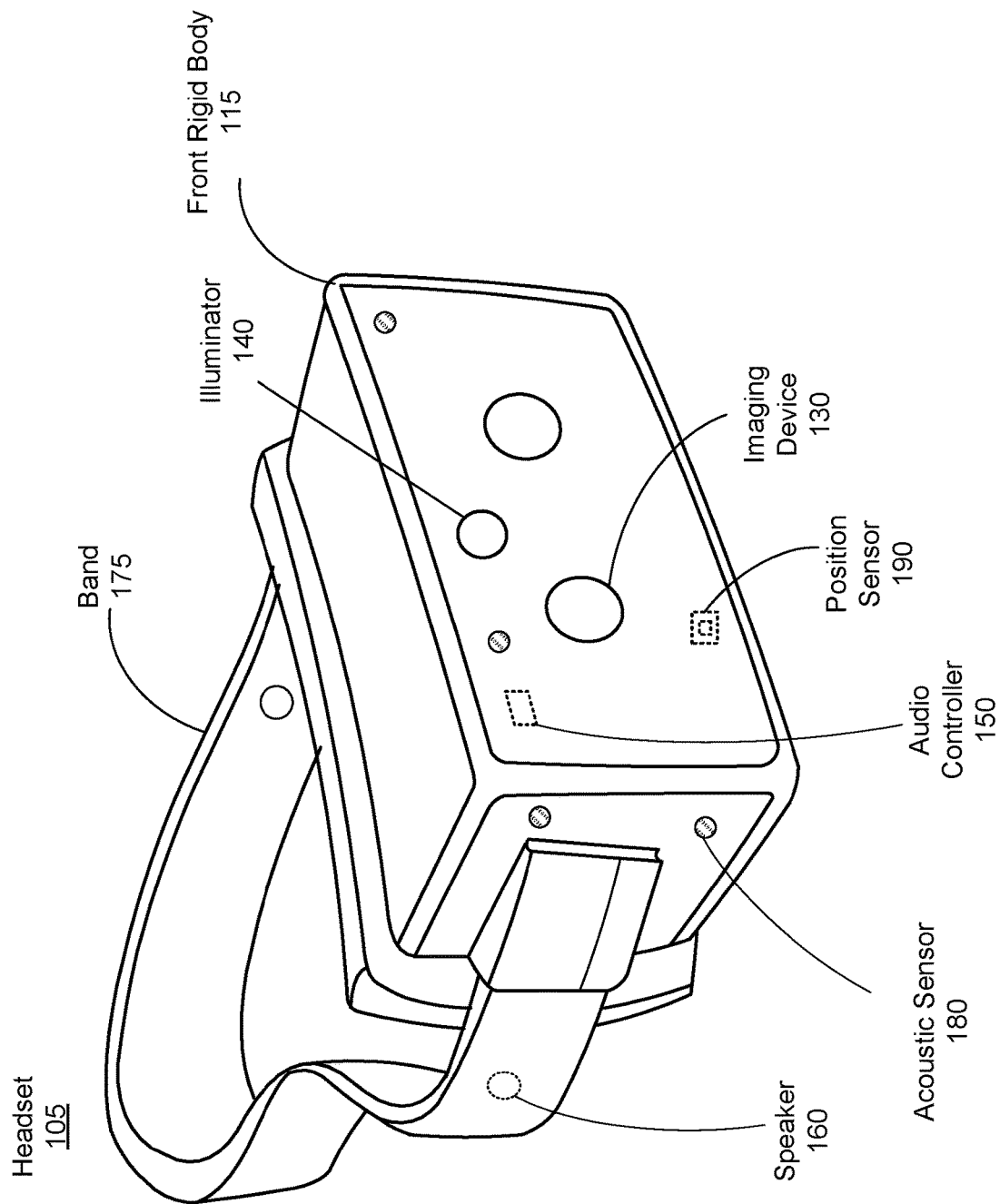
FIG. 1B is a perspective view of a headset implemented as a head-mounted display, in accordance with one or more embodiments.

FIG. 1B is a perspective view of a headset 105 implemented as a HMD, in accordance with one or more embodiments. In embodiments that describe an AR system and/or a MR system, portions of a front side of the HMD are at least partially transparent in the visible band (~380 nm to 750 nm), and portions of the HMD that are between the front side of the HMD and an eye of the user are at least partially transparent (e.g., a partially transparent electronic display). The HMD includes a front rigid body 115 and a band 175. The headset 105 includes many of the same components described above with reference to FIG. 1A, but modified to integrate with the HMD form factor. For example, the HMD includes a display assembly, a DCA, an audio system, and a position sensor 190. FIG. 1B shows the illuminator 140, a plurality of the speakers 160, a plurality of the imaging devices 130, a plurality of acoustic sensors 180, and the position sensor 190. The speakers 160 may be located in various locations, such as coupled to the band 175 (as shown), coupled to front rigid body 115, or may be configured to be inserted within the ear canal of a user.

Figure 2:
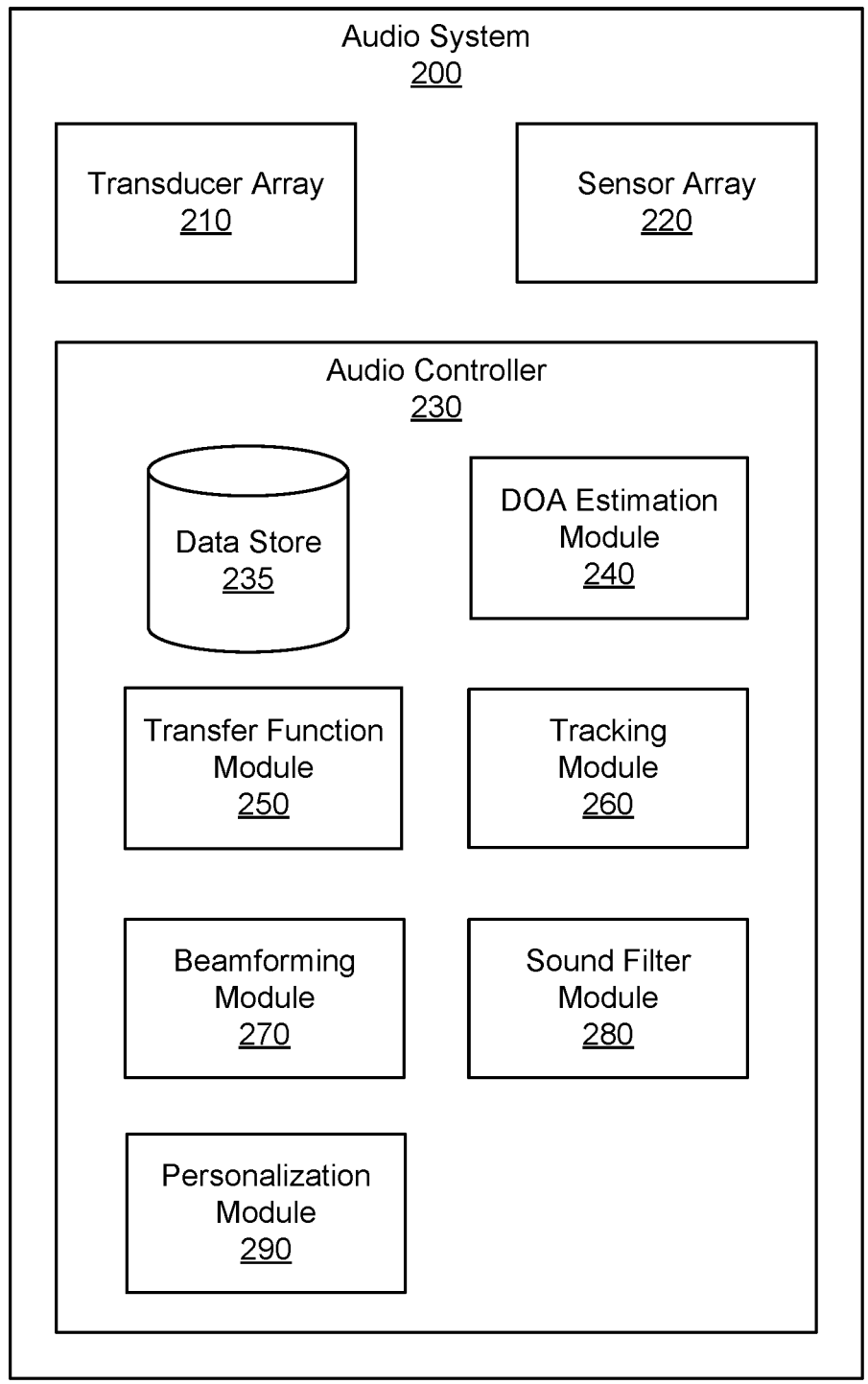
FIG. 2 is a block diagram of an audio system, in accordance with one or more embodiments.

FIG. 2 is a block diagram of an audio system 200, in accordance with one or more embodiments. The audio system in FIG. 1A or FIG. 1B may be an embodiment of the audio system 200. The audio system 200 generates a custom audio profile for a user. The audio system 200 may then use the audio profile to generate audio content for the user. In the embodiment of FIG. 2, the audio system 200 includes a transducer array 210, a sensor array 220, and an audio controller 230. Some embodiments of the audio system 200 have different components than those described here. Similarly, in some cases, functions can be distributed among the components in a different manner than is described here.

The transducer array 210 is configured to present audio content. The transducer array 210 includes a plurality of transducers. A transducer is a device that provides audio content. A transducer may be, e.g., a speaker (e.g., the speaker 160), a tissue transducer (e.g., the tissue transducer 170), some other device that provides audio content, or some combination thereof. A tissue transducer may be configured to function as a bone conduction transducer or a cartilage conduction transducer. The transducer array 210 may present audio content via air conduction (e.g., via one or more speakers), via bone conduction (via one or more bone conduction transducer), via cartilage conduction audio system (via one or more cartilage conduction transducers), or some combination thereof. In some embodiments, the transducer array 210 may include one or more transducers to cover different parts of a frequency range. For example, a piezoelectric transducer may be used to cover a first part of a frequency range and a moving coil transducer may be used to cover a second part of a frequency range.

The bone conduction transducers generate acoustic pressure waves by vibrating bone/tissue in the user's head. A bone conduction transducer may be coupled to a portion of a headset, and may be configured to be behind the auricle coupled to a portion of the user's skull. The bone conduction transducer receives vibration instructions from the audio controller 230, and vibrates a portion of the user's skull based on the received instructions. The vibrations from the bone conduction transducer generate a tissue-borne acoustic pressure wave that propagates toward the user's cochlea, bypassing the eardrum.

The cartilage conduction transducers generate acoustic pressure waves by vibrating one or more portions of the auricular cartilage of the ears of the user. A cartilage conduction transducer may be coupled to a portion of a headset, and may be configured to be coupled to one or more portions of the auricular cartilage of the ear. For example, the cartilage conduction transducer may couple to the back of an auricle of the ear of the user. The cartilage conduction transducer may be located anywhere along the auricular cartilage around the outer ear (e.g., the pinna, the tragus, some other portion of the auricular cartilage, or some combination thereof). Vibrating the one or more portions of auricular cartilage may generate: airborne acoustic pressure waves outside the ear canal; tissue born acoustic pressure waves that cause some portions of the ear canal to vibrate thereby generating an airborne acoustic pressure wave within the ear canal; or some combination thereof. The generated airborne acoustic pressure waves propagate down the ear canal toward the ear drum.

The transducer array 210 generates audio content in accordance with instructions from the audio controller 230. The audio content may be generated in conjunction with an audio assessment routine. In some embodiments, the audio content is spatialized. Spatialized audio content is audio content that appears to originate from a particular direction and/or target region (e.g., an object in the local area and/or a virtual object). For example, spatialized audio content can make it appear that sound is originating from a virtual singer across a room from a user of the audio system 200. The transducer array 210 may be coupled to a wearable device (e.g., the headset 100 or the headset 105). In alternate embodiments, the transducer array 210 may be a plurality of speakers that are separate from the wearable device (e.g., coupled to an external console).

The sensor array 220 detects sounds within a local area surrounding the sensor array 220. The sensor array 220 may include a plurality of acoustic sensors that each detect air pressure variations of a sound wave and convert the detected sounds into an electronic format (analog or digital). The plurality of acoustic sensors may be positioned on a headset (e.g., headset 100 and/or the headset 105), on a user (e.g., in an ear canal of the user), on a neckband, or some combination thereof. An acoustic sensor may be, e.g., a microphone, a vibration sensor, an accelerometer, or any combination thereof. In some embodiments, the sensor array 220 is configured to monitor the audio content generated by the transducer array 210 using at least some of the plurality of acoustic sensors. Increasing the number of sensors may improve the accuracy of information (e.g., directionality) describing a sound field produced by the transducer array 210 and/or sound from the local area.

The audio controller 230 controls operation of the audio system 200. In the embodiment of FIG. 2, the audio controller 230 includes a data store 235, a DOA estimation module 240, a transfer function module 250, a tracking module 260, a beamforming module 270, a sound filter module 280, and a personalization module 290. The audio controller 230 may be located inside a wearable device, such as a headset. Some embodiments of the audio controller 230 have different components than those described here. Similarly, functions can be distributed among the components in different manners than described here. For example, some functions of the controller may be performed external to the headset.

The data store 235 stores data for use by the audio system 200. Data in the data store 235 may include sounds recorded in the local area of the audio system 200, audio content, head-related transfer functions (HRTFs), transfer functions for one or more sensors, array transfer functions (ATFs) for one or more of the acoustic sensors, sound source locations, virtual model of local area, direction of arrival estimates, sound filters, and other data relevant for use by the audio system 200, or any combination thereof. The data store 235 may include audio profiles for one or more users, instructions for audio assessment routines, user response data for the audio assessment routines, etc.

The DOA estimation module 240 is configured to localize sound sources in the local area based in part on information from the sensor array 220. Localization is a process of determining where sound sources are located relative to the user of the audio system 200. The DOA estimation module 240 performs a DOA analysis to localize one or more sound sources within the local area. The DOA analysis may include analyzing the intensity, spectra, and/or arrival time of each sound at the sensor array 220 to determine the direction from which the sounds originated. In some cases, the DOA analysis may include any suitable algorithm for analyzing a surrounding acoustic environment in which the audio system 200 is located.

For example, the DOA analysis may be designed to receive input signals from the sensor array 220 and apply digital signal processing algorithms to the input signals to estimate a direction of arrival. These algorithms may include, for example, delay and sum algorithms where the input signal is sampled, and the resulting weighted and delayed versions of the sampled signal are averaged together to determine a DOA. A least mean squared (LMS) algorithm may also be implemented to create an adaptive filter. This adaptive filter may then be used to identify differences in signal intensity, for example, or differences in time of arrival. These differences may then be used to estimate the DOA. In another embodiment, the DOA may be determined by converting the input signals into the frequency domain and selecting specific bins within the time-frequency (TF) domain to process. Each selected TF bin may be processed to determine whether that bin includes a portion of the audio spectrum with a direct path audio signal. Those bins having a portion of the direct-path signal may then be analyzed to identify the angle at which the sensor array 220 received the direct-path audio signal. The determined angle may then be used to identify the DOA for the received input signal. Other algorithms not listed above may also be used alone or in combination with the above algorithms to determine DOA.

In some embodiments, the DOA estimation module 240 may also determine the DOA with respect to an absolute position of the audio system 200 within the local area. The position of the sensor array 220 may be received from an external system (e.g., some other component of a headset, an artificial reality console, a mapping server, a position sensor (e.g., the position sensor 190), etc.). The external system may create a virtual model of the local area, in which the local area and the position of the audio system 200 are mapped. The received position information may include a location and/or an orientation of some or all of the audio system 200 (e.g., of the sensor array 220). The DOA estimation module 240 may update the estimated DOA based on the received position information.

The transfer function module 250 is configured to generate one or more acoustic transfer functions. Generally, a transfer function is a mathematical function giving a corresponding output value for each possible input value. Based on parameters of the detected sounds, the transfer function module 250 generates one or more acoustic transfer functions associated with the audio system. The acoustic transfer functions may be array transfer functions (ATFs), head-related transfer functions (HRTFs), other types of acoustic transfer functions, or some combination thereof. An ATF characterizes how the microphone receives a sound from a point in space.

An ATF includes a number of transfer functions that characterize a relationship between the sound sources and the corresponding sound received by the acoustic sensors in the sensor array 220. Accordingly, for a sound source there is a corresponding transfer function for each of the acoustic sensors in the sensor array 220. And collectively the set of transfer functions is referred to as an ATF. Accordingly, for each sound source there is a corresponding ATF. Note that the sound source may be, e.g., someone or something generating sound in the local area, the user, or one or more transducers of the transducer array 210. The ATF for a particular sound source location relative to the sensor array 220 may differ from user to user due to a person's anatomy (e.g., ear shape, shoulders, etc.) that affects the sound as it travels to the person's ears. Accordingly, the ATFs of the sensor array 220 are personalized for each user of the audio system 200.

In some embodiments, the transfer function module 250 determines one or more HRTFs for a user of the audio system 200. The HRTF characterizes how an ear receives a sound from a point in space. The HRTF for a particular source location relative to a person is unique to each ear of the person (and is unique to the person) due to the person's anatomy (e.g., ear shape, shoulders, etc.) that affects the sound as it travels to the person's ears. In some embodiments, the transfer function module 250 may determine HRTFs for the user using a calibration process.

In some embodiments, the transfer function module 250 may provide the ATFs and HRTFs to the personalization module 290 to be combined with audio assessment data in an audio profile for the user.

The tracking module 260 is configured to track locations of one or more sound sources. The tracking module 260 may compare current DOA estimates and compare them with a stored history of previous DOA estimates. In some embodiments, the audio system 200 may recalculate DOA estimates on a periodic schedule, such as once per second, or once per millisecond. The tracking module may compare the current DOA estimates with previous DOA estimates, and in response to a change in a DOA estimate for a sound source, the tracking module 260 may determine that the sound source moved. In some embodiments, the tracking module 260 may detect a change in location based on visual information received from the headset or some other external source. The tracking module 260 may track the movement of one or more sound sources over time. The tracking module 260 may store values for a number of sound sources and a location of each sound source at each point in time. In response to a change in a value of the number or locations of the sound sources, the tracking module 260 may determine that a sound source moved. The tracking module 260 may calculate an estimate of the localization variance. The localization variance may be used as a confidence level for each determination of a change in movement.

The beamforming module 270 is configured to process one or more ATFs to selectively emphasize sounds from sound sources within a certain area while de-emphasizing sounds from other areas. In analyzing sounds detected by the sensor array 220, the beamforming module 270 may combine information from different acoustic sensors to emphasize sound associated from a particular region of the local area while deemphasizing sound that is from outside of the region. The beamforming module 270 may isolate an audio signal associated with sound from a particular sound source from other sound sources in the local area based on, e.g., different DOA estimates from the DOA estimation module 240 and the tracking module 260. The beamforming module 270 may thus selectively analyze discrete sound sources in the local area. In some embodiments, the beamforming module 270 may enhance a signal from a sound source. For example, the beamforming module 270 may apply sound filters which eliminate signals above, below, or between certain frequencies. Signal enhancement acts to enhance sounds associated with a given identified sound source relative to other sounds detected by the sensor array 220. In some embodiments, based on parameters received from the personalization module 290, the beamforming module 270 may adjust the width or behavior of a beam in noisy environments according to the user's estimated speech understanding or listening effort.

The sound filter module 280 determines sound filters for the transducer array 210. In some embodiments, the sound filters cause the audio content to be spatialized, such that the audio content appears to originate from a target region. The sound filter module 280 may use HRTFs and/or acoustic parameters to generate the sound filters. The acoustic parameters describe acoustic properties of the local area. The acoustic parameters may include, e.g., a reverberation time, a reverberation level, a room impulse response, etc. In some embodiments, the sound filter module 280 calculates one or more of the acoustic parameters. In some embodiments, the sound filter module 280 requests the acoustic parameters from a mapping server (e.g., as described below with regard to FIG. 4).

The sound filter module 280 provides the sound filters to the transducer array 210. In some embodiments, the sound filters may cause positive or negative amplification of sounds as a function of frequency. For example, based on parameters received from the personalization module 290, the sound filter module 280 may amplify sounds at certain frequencies which the user does not detect as easily as other frequencies.

The personalization module 290 generates an audio profile for the user. The audio profile describes how a user perceives sounds. The audio profile contains parameters which describe how sound should be presented to the user in order to enhance the audio experience for the user. The parameters may comprise gains and limits for sounds. For example, the parameters may indicate a gain of 6 dB for the frequency band between 10 kHz-15 kHz, up to a maximum limit of 85 dB sound pressure level, such that the audio system increases the amplitude of sounds in that frequency band by 6 dB.

In some embodiments, the parameters may comprise scaling factors that indicate that the amplitude of certain frequencies should be increased, or that the amplitude of certain frequencies should be decreased relative to other frequencies (e.g., a scaling factor of 1.2 for the frequency band between 10 kHz-15 kHz may indicate that the audio system should increase the amplitude of sounds in that frequency band by 20%). The parameters may indicate a maximum level of reverberation for an environment that allows speech to be intelligible to the user. The parameters may describe beamformer adjustments, such as width or dynamic behavior, in noisy environments according to the user's estimated speech understanding or listening effort. The parameters may provide artificial exaggeration of sound-source separation to aid in spatial release from masking. The parameters may provide a gain and compression structure tailored to the user's hearing. The parameters may describe how to enhance the sound of other talkers, such as by shifting a frequency, which allows the user to better understand the talker. The sound parameters may include sound localization ability, magnitude of spatial release from masking, binaural masking level difference, speech in noise thresholds for different types of background noise, or any other suitable parameters which may increase the audio quality for a user.

The audio system 200 modifies sounds presented to the user according to the parameters in the audio file to provide an enhanced audio experience for the user. For example, the parameters in the audio profile may indicate that the audio system should increase or decrease the amplitude of certain frequencies presented to the user.

In order to generate the audio profile for the user, the personalization module 290 conducts an active and/or passive audio assessment for the user. For example, the personalization module 290 may present the user with audio games, an audiology screen, listening tests, momentary environmental assessments, and post experience surveys.

The audio assessment may include an audio assessment routine. The audio assessment routine is a series of steps by which the audio system determines parameters describing the characteristics of a user's hearing, such as hyperacusis or presbyacusis to certain frequencies, acceptable reverberation levels, etc. For example, the audio assessment routines may comprise explicit listening test routines, including traditional audiology, speech in noise tests, audio games, spatial resolution tests, listening effort, localization accuracy, performance monitoring, and post experience surveys. The audio assessment routines result in audio assessment data describing the user's responses to the audio assessment routines. For example, the audio assessment data may comprise binary data indicating whether the user reacted to a sound, accuracy values indicating how well the user understood speech in different noise environments, duration and smoothness of orientation movements toward sound sources, proportion of front/back confusions, localization errors, minimum audible angles, degree of binaural masking level difference, etc.

The personalization module 290 stores the audio assessment data in an audio profile. In some embodiments, the audio profile may be stored locally on the wearable device, such as in the data store 235. In some embodiments, the personalization module 290 may transmit the assessment data or the audio profile to an external system, such as a social networking system. The personalization module 290 may continuously update the audio profile as additional assessment data is captured.

In some embodiments, the personalization module 290 obtains perceptual feedback from the user as part of the audio assessment routine. The perceptual feedback may indicate whether the user responded to a sound, whether the user understood speech in audio content, or indicate a perceived location of the synthesized sound. In some embodiments, the perceptual feedback may comprise a gaze direction of the user's eyes, indicating that the user perceived a sound emanating from the gaze direction. The perceptual feedback may comprise a spoken response from the user, such as "front," "back," "left," or "right," or a repetition by the user of a phrase that is presented to the user. The perceptual feedback may comprise a movement by the user, such as the user turning their head or pointing a hand in a direction.

The personalization module 290 captures active and passive responses from the user. The responses may be captured by any sensors on the headset, such as via microphone, hand-tracking, controller, pupillometry, electroencephalography (EEG), galvanic skin response (GSR), the eye tracking module, by haptic feedback from a glove, by positions sensors that capture motion of the headset such as IMUS, etc. In some embodiments, the perceptual feedback may be captured by external sensors, such as by cameras which detect the position of the headset or the user.

In some embodiments, the perceptual feedback may be obtained in an active assessment routine. For example, the headset may inform the user that an audio assessment is taking place, and the headset may provide an audio and/or visual instruction to perform an action, such as to repeat a phrase or look in the direction of a sound.

In some embodiments, the perceptual feedback may be obtained in a passive assessment routine, in which the user may be unaware that the audio assessment is being conducted. For example, the user may be interacting with a headset, such as participating in a virtual reality game, and the personalization module 290 may monitor the user responses to sounds during the course of the virtual reality game.

The personalization module 290 compares the perceptual feedback for each sound source in an audio assessment routine to one or more properties of the sound source. One or more sound sources may be generated by the audio system for the audio assessment routine. The sound sources generated by the audio system may have known properties. One or more sound sources may be generated by objects or people in the local area. The audio system may determine properties for sound sources, such as tracking the location and measuring the frequencies, and compare the user responses to the measured properties. The properties of the sound source may include location, amplitude, frequency, words in speech, etc.

The personalization module 290 may determine an accuracy value for one or more properties of each sound source. For example, the personalization module 290 may assign a scalar accuracy value between 1-10, with 10 indicating a highly accurate user response to the sound source. Each sound source may include an accuracy value for each property. For example, a first accuracy value for a sound source may indicate how well the user understood the words in a phrase, and a second accuracy value may indicate a difference in the user's perceived location of a sound source to the actual or intended location of a sound source.

The personalization module 290 analyzes the results of the audio assessment to create the audio profile. In some embodiments, the personalization module 290 analyzes the results locally on the headset. In some embodiments, the personalization module 290 transmits the results to an external system, and the external system generates the audio profile.

The audio profile may describe environmental conditions associated with positive or negative assessment data for the user. For example, the environmental conditions may include the geometric conditions of a room or local area, GPS coordinates, time of day, language being spoken, signal to noise ratio, reverberation, background noise characteristics, etc. The audio profile may indicate whether the user was able or unable to understand speech in specific environmental conditions.

Additionally, the audio profile may comprise results related to physical characteristics of the user that influence hearing, such as personalized HRTFs and Body-related Transfer Functions, to generate the customized audio profile. The physical data may describe the shape of the user's head, ears, and torso. The physical data may be obtained from pictures of the user captured by the wearable device, or retrieved from a database, such as from a social networking system. The audio profile may include HRTFs generated based in part on the shapes. The audio profile may use the HRTFs in conjunction with the audio assessment data to provide instructions for subsequent presentation of sounds for the user. For example, an HRTF for a sound source at a particular angle may attenuate some frequencies more than others, which could potentially render a frequency inaudible to the user. However, based on the audio assessment data, the audio profile may indicate the frequency should be increased to a dB level which is audible to the user. Thus, by combining the HRTFs with the audio assessment data, the audio profile may contain a complete set of parameters for improving the audio experience of the user.

In some embodiments, the personalization module 290 may store the audio profile locally on the headset, such as in the data store 235. In some embodiments, the personalization module 290 may transmit the audio profile to an external system, and the external system may store the audio profile in a database. For example, the audio profile may be stored in a database of a social network and associated with a user account.

In response to the audio controller 230 determining to present audio content to the user, the audio controller 230 queries the personalization module 290 for parameters in an audio profile. The personalization module 290 retrieves the audio profile for the user, such as by querying the data store 235, or by querying an external system.

The personalization module 290 uses the audio profile to modify sounds presented to the user. Using the audio profile may improve the audio across all of the user's audio experiences, including video calling, virtual reality games and applications, augmented reality telepresence, real-time speech enhancement, real-time noise reduction, etc. For example, during a video call, the personalization module 290 may increase the amplitude of talkers who speak in certain frequency ranges if the parameters in the audio profile indicate that the user has low sensitivity in those frequency ranges. For a virtual reality game, if the parameters in the audio file indicate that the user has difficulty understanding speech in reverberant environments, the personalization module 290 may decrease the amount of reverberations in sounds presented to the user. The personalization module 290 may provide the parameters or instructions based on the parameters to the sound filter module 280 to adjust the sound filters according to the parameters.

In some embodiments, the personalization module 290 may store an enhancement scheme associated with the audio profile in the data store 235. The enhancement scheme is a predefined set of parameters used to modify sounds for a user. The enhancement scheme may be used in place of the parameters in an audio profile for a user. Different users may have similar hearing characteristics, such that the different users may benefit from similar modifications to sound presented to the users. By grouping multiple users into subsets associated with an enhancement scheme, the system may decrease the complexity and processing power used to generate an enhanced audio experience for the user. For example, in some embodiments, the system may comprise ten different enhancement schemes, or one thousand different enhancement schemes, and one of the enhancement schemes may be assigned to the audio profile based on a similarity between the user's assessment data and the selected enhancement scheme.

In response to the audio system 200 detecting a new user, the audio system 200 may attempt to retrieve an audio profile for the new user. The audio system 200 may identify the new user based on, for example, login information, passwords, facial recognition, etc. In some embodiments, the user may provide the user's social network identification to the audio system 200. The personalization module 290 may query the data store 235 or an external system for an audio profile for the new user. If the data store 235 or external system identifies an audio profile for the new user, the data store 235 or the external system may transmit the audio profile to the audio system 200. If the personalization module 290 is unable to obtain an audio profile for the new user, the personalization module 290 may initiate an audio assessment for the new user in order to generate an audio profile.

Systems and applications which present sounds to the user may access the audio profile and modify the sounds presented to the user based on the data in the audio profile to enhance the audio experience for the user. The headset, the external system, or a third-party application may access the audio profile to generate sound for the user of the headset. For example, the user may access third-party audio content, such as a gaming application or website, using any device available to the user. The user may provide the third-party with a user ID for a social network, and the third-party system may query the social network for an audio file of the user. The third-party system may modify the audio content presented to the user according to the parameters in the audio file.

The audio profile may comprise security settings. The security settings may only allow authorized parties access to the audio profile, or to only allow access to certain portions of the data stored in the audio profile. For example, the audio profile may be stored on a social network in conjunction with a user profile of the user, and the security settings may indicate that only entities which have a connection with the user in the social network may access the user's audio profile. In some embodiments, the data in the audio profile may be encrypted, and the encryption key may be stored on the user's wearable device, such third-party systems may utilize the audio profile to present content to the user on the user's device, without providing the third-party system with access to the contents of the audio profile.

Figure 3:
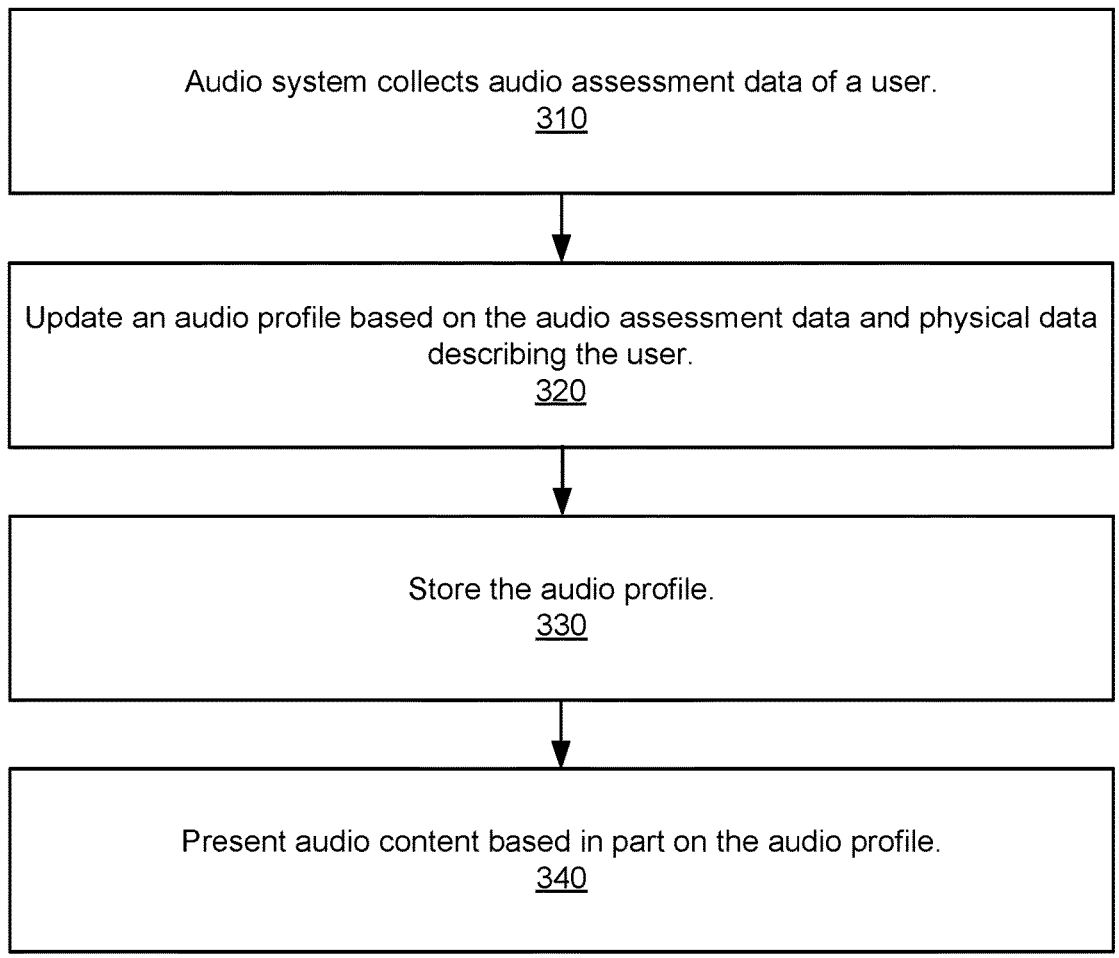
FIG. 3 illustrates a flowchart of a process for providing personalized audio enhancement, in accordance with one or more embodiments.

FIG. 3 is a flowchart of a method 300 of generating enhanced audio content, in accordance with one or more embodiments. The process shown in FIG. 3 may be performed by components of an audio system (e.g., audio system 200). Other entities may perform some or all of the steps in FIG. 3 in other embodiments. Embodiments may include different and/or additional steps, or perform the steps in different orders.

An audio system on a wearable device collects 310 audio assessment data of a user. Collecting the audio assessment data may comprise performing an audio assessment routine. The audio assessment routine may include monitoring user responses to audio content. For example, the user may repeat a phrase, provide a rating for audio content, look in the direction of a sound source, etc.

The audio system updates 320 an audio profile based on the audio assessment data and physical data describing the user. The audio profile may include parameters indicating how to adjust audio content for presentation to the user. For example, based on the results of the audio assessment routine, the parameters may indicate that the amplitude of certain frequency bands should be increased for the user, or that the level of reverberation in artificial audio environments should be decreased to permit the user to understand speech. The physical data may describe the shape of the user's head, ears, and torso. The physical data may be obtained from pictures of the user captured by the wearable device, or retrieved from a database, such as from a social networking system. The audio profile may include HRTFs generated based in part on the shapes.

The audio system stores 330 the audio profile. In some embodiments, the audio system stores the audio profile locally on the wearable device. In other embodiments, the audio system may transmit the audio profile to an external system, such as a social media network, and the external system may store the audio profile with a user profile for the user. The audio system or the external system may assign an enhancement scheme to the audio profile.

The audio system presents 340 audio content to the user based in part on the audio profile. The audio content may include audio for a virtual reality game, sounds generated by objects in the local area of the user, music, or any other audio suitable for generation by a wearable device. The audio system may modify the audio content based on the parameters within the audio profile. In some embodiments, the audio system may modify the audio content based on the enhancement scheme associated with the audio file.

In some embodiments, the audio content may be presented to the user by any device, such as a device which the user has not previously used. The device may request the audio profile from the external system, and the device may present audio content customized to the user based on the audio profile.

Figure 4:
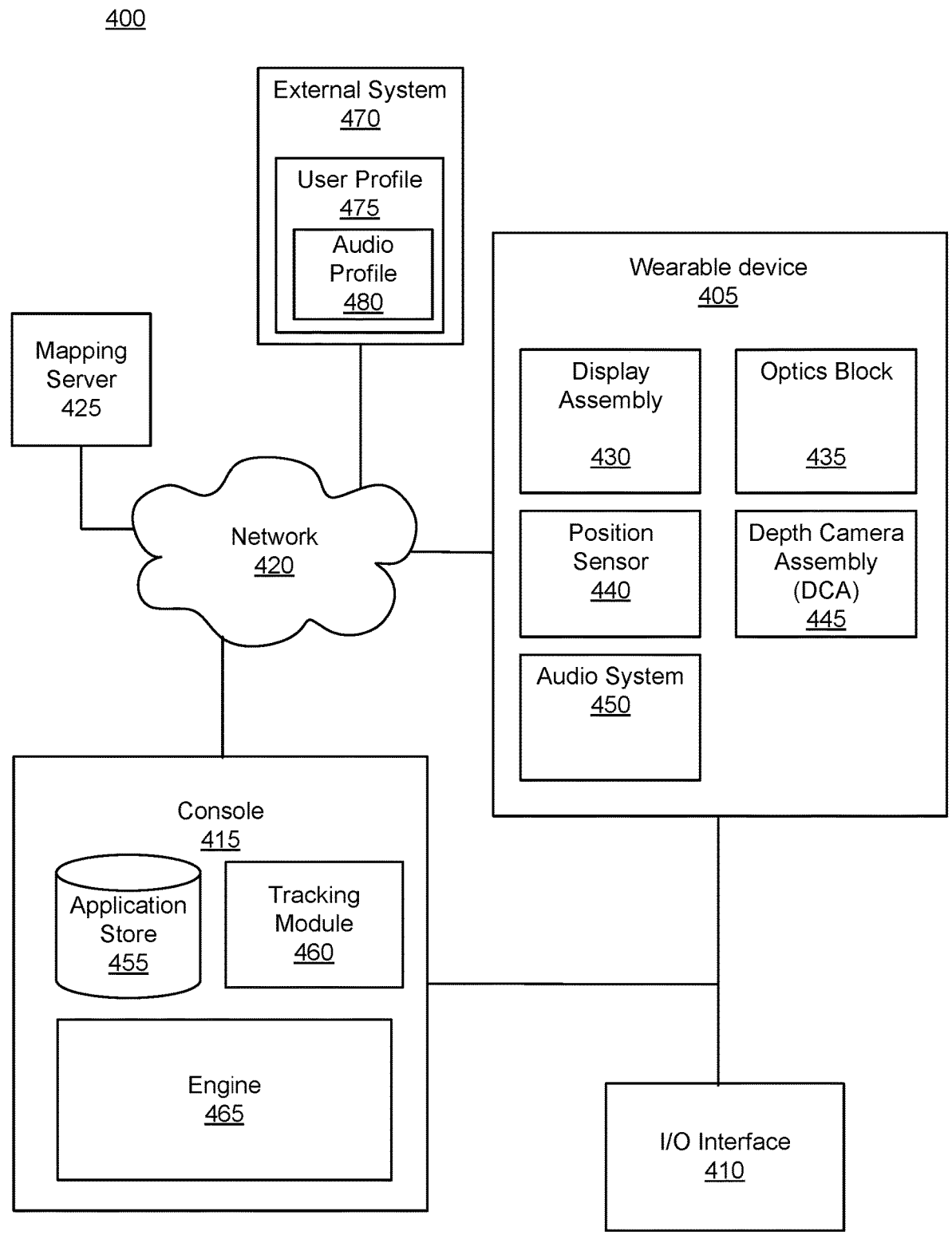
FIG. 4 is a system that includes a headset, in accordance with one or more embodiments.

FIG. 4 is a system 400 that includes a wearable device 405, in accordance with one or more embodiments. In some embodiments, the wearable device 405 may be the headset 100 of FIG. 1A or the headset 105 of FIG. 1B. The system 400 may operate in an artificial reality environment (e.g., a virtual reality environment, an augmented reality environment, a mixed reality environment, or some combination thereof). The system 400 shown by FIG. 4 includes the wearable device 405, an input/output (I/O) interface 410 that is coupled to a console 415, the network 420, the mapping server 425, and the external system 470. While FIG. 4 shows an example system 400 including one wearable device 405 and one I/O interface 410, in other embodiments any number of these components may be included in the system 400. For example, there may be multiple headsets each having an associated I/O interface 410, with each headset and I/O interface 410 communicating with the console 415. In alternative configurations, different and/or additional components may be included in the system 400. Additionally, functionality described in conjunction with one or more of the components shown in FIG. 4 may be distributed among the components in a different manner than described in conjunction with FIG. 4 in some embodiments. For example, some or all of the functionality of the console 415 may be provided by the wearable device 405.

The wearable device 405 includes the display assembly 430, an optics block 435, one or more position sensors 440, and the DCA 445. Some embodiments of wearable device 405 have different components than those described in conjunction with FIG. 4. Additionally, the functionality provided by various components described in conjunction with FIG. 4 may be differently distributed among the components of the wearable device 405 in other embodiments, or be captured in separate assemblies remote from the wearable device 405.

The display assembly 430 displays content to the user in accordance with data received from the console 415. The display assembly 430 displays the content using one or more display elements (e.g., the display elements 120). A display element may be, e.g., an electronic display. In various embodiments, the display assembly 430 comprises a single display element or multiple display elements (e.g., a display for each eye of a user). Examples of an electronic display include: a liquid crystal display (LCD), an organic light emitting diode (OLED) display, an active-matrix organic light-emitting diode display (AMOLED), a waveguide display, some other display, or some combination thereof. Note in some embodiments, the display element 120 may also include some or all of the functionality of the optics block 435.

The optics block 435 may magnify image light received from the electronic display, corrects optical errors associated with the image light, and presents the corrected image light to one or both eyeboxes of the wearable device 405. In various embodiments, the optics block 435 includes one or more optical elements. Example optical elements included in the optics block 435 include: an aperture, a Fresnel lens, a convex lens, a concave lens, a filter, a reflecting surface, or any other suitable optical element that affects image light. Moreover, the optics block 435 may include combinations of different optical elements. In some embodiments, one or more of the optical elements in the optics block 435 may have one or more coatings, such as partially reflective or anti-reflective coatings.

Magnification and focusing of the image light by the optics block 435 allows the electronic display to be physically smaller, weigh less, and consume less power than larger displays. Additionally, magnification may increase the field of view of the content presented by the electronic display. For example, the field of view of the displayed content is such that the displayed content is presented using almost all (e.g., approximately 110 degrees diagonal), and in some cases all, of the user's field of view. Additionally, in some embodiments, the amount of magnification may be adjusted by adding or removing optical elements.

In some embodiments, the optics block 435 may be designed to correct one or more types of optical error. Examples of optical error include barrel or pincushion distortion, longitudinal chromatic aberrations, or transverse chromatic aberrations. Other types of optical errors may further include spherical aberrations, chromatic aberrations, or errors due to the lens field curvature, astigmatisms, or any other type of optical error. In some embodiments, content provided to the electronic display for display is pre-distorted, and the optics block 435 corrects the distortion when it receives image light from the electronic display generated based on the content.

The position sensor 440 is an electronic device that generates data indicating a position of the wearable device 405. The position sensor 440 generates one or more measurement signals in response to motion of the wearable device 405. The position sensor 190 is an embodiment of the position sensor 440. Examples of a position sensor 440 include: one or more IMUs, one or more accelerometers, one or more gyroscopes, one or more magnetometers, another suitable type of sensor that detects motion, or some combination thereof. The position sensor 440 may include multiple accelerometers to measure translational motion (forward/back, up/down, left/right) and multiple gyroscopes to measure rotational motion (e.g., pitch, yaw, roll). In some embodiments, an IMU rapidly samples the measurement signals and calculates the estimated position of the wearable device 405 from the sampled data. For example, the IMU integrates the measurement signals received from the accelerometers over time to estimate a velocity vector and integrates the velocity vector over time to determine an estimated position of a reference point on the wearable device 405. The reference point is a point that may be used to describe the position of the wearable device 405. While the reference point may generally be defined as a point in space, however, in practice the reference point is defined as a point within the wearable device 405.

The DCA 445 generates depth information for a portion of the local area. The DCA includes one or more imaging devices and a DCA controller. The DCA 445 may also include an illuminator. Operation and structure of the DCA 445 is described above with regard to FIG. 1A.

The audio system 450 provides audio content to a user of the wearable device 405. The audio system 450 may be an embodiment of the audio system 200 described above. The audio system 450 may comprise one or acoustic sensors, one or more transducers, and an audio controller. The audio system 450 may provide spatialized audio content to the user. In some embodiments, the audio system 450 may request acoustic parameters from the mapping server 425 over the network 420. The acoustic parameters describe one or more acoustic properties (e.g., room impulse response, a reverberation time, a reverberation level, etc.) of the local area. The audio system 450 may provide information describing at least a portion of the local area from e.g., the DCA 445 and/or location information for the wearable device 405 from the position sensor 440. The audio system 450 may generate one or more sound filters using one or more of the acoustic parameters received from the mapping server 425, and use the sound filters to provide audio content to the user.

The audio system 450 may conduct an audio assessment routine. The audio system 450 may create an audio profile 480 for the user based on the audio assessment routine. The audio system 450 may transmit the audio profile 480 and/or the results of the audio assessment routine to the external system 470, and the external system 470 may store the audio profile 480. In some embodiments, the audio system 450 may request an audio profile for the user from the external system 470. The audio system 450 may modify audio content being presented to the user based on the parameters stored in the audio profile.

The I/O interface 410 is a device that allows a user to send action requests and receive responses from the console 415. An action request is a request to perform a particular action. For example, an action request may be an instruction to start or end capture of image or video data, or an instruction to perform a particular action within an application. The I/O interface 410 may include one or more input devices. Example input devices include: a keyboard, a mouse, a game controller, or any other suitable device for receiving action requests and communicating the action requests to the console 415. An action request received by the I/O interface 410 is communicated to the console 415, which performs an action corresponding to the action request. In some embodiments, the I/O interface 410 includes an IMU that captures calibration data indicating an estimated position of the I/O interface 410 relative to an initial position of the I/O interface 410. In some embodiments, the I/O interface 410 may provide haptic feedback to the user in accordance with instructions received from the console 415. For example, haptic feedback is provided when an action request is received, or the console 415 communicates instructions to the I/O interface 410 causing the I/O interface 410 to generate haptic feedback when the console 415 performs an action.

The console 415 provides content to the wearable device 405 for processing in accordance with information received from one or more of: the DCA 445, the wearable device 405, and the I/O interface 410. In the example shown in FIG. 4, the console 415 includes an application store 455, a tracking module 460, and an engine 465. Some embodiments of the console 415 have different modules or components than those described in conjunction with FIG. 4. Similarly, the functions further described below may be distributed among components of the console 415 in a different manner than described in conjunction with FIG. 4. In some embodiments, the functionality discussed herein with respect to the console 415 may be implemented in the wearable device 405, or a remote system.

The application store 455 stores one or more applications for execution by the console 415. An application is a group of instructions, that when executed by a processor, generates content for presentation to the user. Content generated by an application may be in response to inputs received from the user via movement of the wearable device 405 or the I/O interface 410. Examples of applications include: gaming applications, conferencing applications, video playback applications, or other suitable applications. In some embodiments, one or more applications may be stored on an external server, which communicates with the console 415 or the wearable device 405 over the network 420. The application may generate audio content for presentation on the wearable device 405, and the audio system 450 may modify the audio content based on the audio profile 485. In some embodiments, the application transmits audio content to the audio system 450, and the audio system 450 modifies the audio content based on the parameters in an audio file stored locally on the wearable device 405.

The tracking module 460 tracks movements of the wearable device 405 or of the I/O interface 410 using information from the DCA 445, the one or more position sensors 440, or some combination thereof. For example, the tracking module 460 determines a position of a reference point of the wearable device 405 in a mapping of a local area based on information from the wearable device 405. The tracking module 460 may also determine positions of an object or virtual object. Additionally, in some embodiments, the tracking module 460 may use portions of data indicating a position of the wearable device 405 from the position sensor 440 as well as representations of the local area from the DCA 445 to predict a future location of the wearable device 405. The tracking module 460 provides the estimated or predicted future position of the wearable device 405 or the I/O interface 410 to the engine 465.

The engine 465 executes applications and receives position information, acceleration information, velocity information, predicted future positions, or some combination thereof, of the wearable device 405 from the tracking module 460. Based on the received information, the engine 465 determines content to provide to the wearable device 405 for presentation to the user. For example, if the received information indicates that the user has looked to the left, the engine 465 generates content for the wearable device 405 that mirrors the user's movement in a virtual local area or in a local area augmenting the local area with additional content. Additionally, the engine 465 performs an action within an application executing on the console 415 in response to an action request received from the I/O interface 410 and provides feedback to the user that the action was performed. The provided feedback may be visual or audible feedback via the wearable device 405 or haptic feedback via the I/O interface 410.

The network 420 couples the wearable device 405 and/or the console 415 to the mapping server 425. The network 420 may include any combination of local area and/or wide area networks using both wireless and/or wired communication systems. For example, the network 420 may include the Internet, as well as mobile telephone networks. In one embodiment, the network 420 uses standard communications technologies and/or protocols. Hence, the network 420 may include links using technologies such as Ethernet, 802.11, worldwide interoperability for microwave access (WiMAX), 2G/3G/4G mobile communications protocols, digital subscriber line (DSL), asynchronous transfer mode (ATM), InfiniBand, PCI Express Advanced Switching, etc. Similarly, the networking protocols used on the network 420 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over the network 420 can be represented using technologies and/or formats including image data in binary form (e.g. Portable Network Graphics (PNG)), hypertext markup language (HTML), extensible markup language (XML), etc. In addition, all or some of links can be encrypted using conventional encryption technologies such as secure sockets layer (SSL), transport layer security (TLS), virtual private networks (VPNs), Internet Protocol security (IPsec), etc.

The mapping server 425 may include a database that stores a virtual model describing a plurality of spaces, wherein one location in the virtual model corresponds to a current configuration of a local area of the wearable device 405. The mapping server 425 receives, from the wearable device 405 via the network 420, information describing at least a portion of the local area and/or location information for the local area. The mapping server 425 determines, based on the received information and/or location information, a location in the virtual model that is associated with the local area of the wearable device 405. The mapping server 425 determines (e.g., retrieves) one or more acoustic parameters associated with the local area, based in part on the determined location in the virtual model and any acoustic parameters associated with the determined location. The mapping server 425 may transmit the location of the local area and any values of acoustic parameters associated with the local area to the wearable device 405.

The external system 470 may be a system that stores user profiles, such as a social network. The external system 470 may store a user profile 475 for the user of the wearable device 405. The user profile 475 may comprise information regarding the user, such as demographic information, content uploaded by the user, connections between the user and other users of the external system 470, etc. The external system 470 may store the audio profile 480 as part of, or associated with, the user profile 475. The audio profile 480 may contain the audio assessment data received from the wearable device 405.

In some embodiments, the external system 470 may store an enhancement scheme associated with the audio profile. The enhancement scheme is a predefined set of parameters used to modify sounds for a user. The enhancement scheme may be used in place of the parameters in an audio file for a user.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method comprising:
   detecting a sound within a local area;
   converting the detected sound into a synthesized sound having an electronic format;
   retrieving an audio profile of a user, wherein,
      the audio profile comprises a plurality of parameters,
      at least one of the plurality of parameters is generated based on a detected gaze direction of the user in response to the synthesized sound, and
      the gaze direction indicates that the user perceived the synthesized sound emanating from the gaze direction;
   modifying audio content including the synthesized sound, based on the plurality of parameters; and
   presenting the modified audio content to the user.

2. The method of claim 1, further comprising retrieving the audio profile from a social network, wherein the social network associates the audio profile with a profile of the user.

3. The method of claim 1, further comprising modifying the audio content further based on an enhancement scheme associated with the audio profile.

4. The method of claim 1, further comprising modifying the audio profile.

5. The method of claim 1, further comprising:
   receiving the audio profile from an external system; and
   modifying the audio content based on the received audio profile.

6. The method of claim 1, further comprising collecting audio assessment data by:
   presenting the synthesized sound to the user; and
   detecting a response to the synthesized sound by the user.

7. The method of claim 6, wherein the collecting the audio assessment data comprises:
   determining a location of a sound source in the local area; and
   detecting a response to the sound source by the user.

8. The method of claim 1, wherein the audio profile comprises physical data describing an ear shape of the user.

9. The method of claim 1, wherein modifying the audio content comprises increasing an amplitude of frequencies within a frequency band.

10. The method of claim 1, wherein the at least one of the plurality of parameters is generated based on an audio assessment routine.

11. The method of claim 1, wherein the plurality of parameters comprise a scaling factor and a maximum level of reverberation.

12. The method of claim 1, wherein the audio profile comprises a security setting, wherein the security setting indicates whether a third-party is authorized to access the audio profile.

13. A computer program product comprising a non-transitory computer-readable storage medium storing a computer program code for:
   detecting a sound within a local area;
   converting the detected sound into a synthesized sound having an electronic format;
   retrieving an audio profile of a user, wherein,
      the audio profile comprises a plurality of parameters,
      at least one of the plurality of parameters is generated based on a detected gaze direction of the user in response to the synthesized sound, and
      the gaze direction indicates that the user perceived the synthesized sound emanating from the gaze direction;
   modifying audio content including the synthesized sound, based on the plurality of parameters; and
   presenting the modified audio content to the user.

14. The computer program product of claim 13, further comprising a computer program code for retrieving the audio profile from a social network, wherein the social network associates the audio profile with a profile of the user.

15. A wearable device comprising a non-transitory computer-readable storage medium storing a computer program code for:
   detecting a sound within a local area;
   converting the detected sound into a synthesized sound having an electronic format;
   retrieving an audio profile of a user, wherein,
      the audio profile comprises a plurality of parameters,
      at least one of the plurality of parameters is generated based on a detected gaze direction of the user in response to the synthesized sound, and
      the gaze direction indicates that the user perceived the synthesized sound emanating from the gaze direction;
   modifying audio content including the synthesized sound, based on the plurality of parameters; and
   presenting the modified audio content to the user.

16. The wearable device of claim 15, further comprising a computer program code for retrieving the audio profile from a social network, wherein the social network associates the audio profile with a profile of the user.

17. The wearable device of claim 15, further comprising a computer program code for modifying the audio content based on an enhancement scheme associated with the audio profile.

18. The wearable device of claim 15, further comprising a computer program code for:
   receiving the audio profile from an external system; and
   modifying the audio content based on the received audio profile.

19. The wearable device of claim 15, further comprising a computer program code for collecting audio assessment data by:
   presenting the synthesized sound to the user; and
   detecting a response to the synthesized sound by the user.

20. The wearable device of claim 19, wherein the collecting the audio assessment data comprises:
   determining a location of a sound source in the local area; and
   detecting a response to the sound source by the user.

* * * * *